United States Patent [19]

Abdulla

[11] 4,013,658

[45] Mar. 22, 1977

[54] SYNTHESIS OF 3,5-DIPHENYL-4(1H)-PYRIDAZINONES

[75] Inventor: Riaz F. Abdulla, Greenfield, Ind.

[73] Assignee: Eli Lilly and Company, Indianapolis, Ind.

[22] Filed: July 3, 1975

[21] Appl. No.: 593,094

[52] U.S. Cl. .................. 260/250 A; 260/240 D; 260/570.5 C; 71/92

[51] Int. Cl.² ......................... C07D 237/14

[58] Field of Search .................. 260/250 A

[56] References Cited

UNITED STATES PATENTS 3,644,355   2/1972   Ebner ..................... 260/250 A

FOREIGN PATENTS OR APPLICATIONS 811,825   4/1974   Belgium
105,446   4/1974   Germany

OTHER PUBLICATIONS

Breslow et al., J. Amer. Chem. Soc. 87, 1320, (1965).
Izzo et al., Chem & Ind. 839–840, (1964).
Hünig et al. Chem. Berichte 93, pp. 909–920, (1960).

*Primary Examiner*—Donald G. Daus
*Assistant Examiner*—Mark L. Berch
*Attorney, Agent, or Firm*—Joseph A. Jones; Everet F. Smith

[57] ABSTRACT

A series of 3,5-diphenyl-4(1H)-pyridazinones are synthesized by a two-step process, both steps of which are new. In the first step, a phenylglyoxyloyl halide is reacted with a styrylamine in the presence of a base to form a 1-amino-2,4-diphenyl-1-buten-3,4-dione. In the second step, the enaminoketone formed in the first step is reacted with hydrazine or an alkylhydrazine to form the pyridazinone. Both steps of the reaction proceed in good yields at temperatures in the range of from about 0° C. to about 40° C. in the common reaction solvents.

4 Claims, No Drawings

“SYNTHESIS OF 3,5-DIPHENYL-4(1H)-PYRIDAZINONES

BACKGROUND OF THE INVENTION

This invention belongs to the art of agricultural organic chemistry, and provides to the art an unusually facile synthesis of herbicidal pyridazinones.

Previous syntheses of pyridazinones have been quite difficult, and have required unusual intermediate compounds. For example, Breslow et al., "Diphenylcyclopropenones", *Chem. & Ind.* 839–40 (1964), disclosed and Izzo et al., "Reaction of Diazomethane with Cyclopropenones", *Chem. J Ind.* 839–40 (1964), disclosed processes for making 3,5-diphenyl-4(1H)-pyridazinone. One of their reaactants, diazomethane, is a hazardous compound, and the other reactant, cyclopropenone, is extremely difficult of access.

SUMMARY OF THE INVENTION

This invention provides to the argicultural chemical art a process for making compounds of the formula

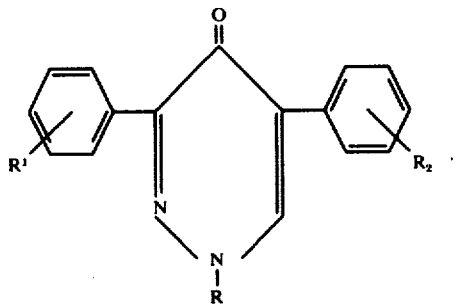

wherein R represents hydrogen or $C_1$–$C_3$ alkyl, and $R^1$ and $R^2$ independently represent trifluoromethyl, hydrogen, fluoro, chloro, bromo or methyl, which process comprises contacting a glyoxyloyl halide of the formula

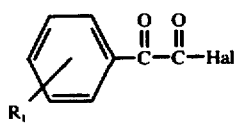

wherein Hal represents fluoro, chloro or bromo, with a styrylamine of the formula

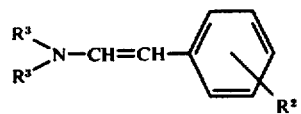

wherein the $R^3$ groups independently represent $C_1$–$C_3$ alkyl, or the $R^3$ groups combine with the nitrogen atom to which they are attached to form azetidino, pyrrolidino, piperidino or morpholino, at a temperature from about 0° C. to about 40° C. in an inert reaction solvent in the presence of a base to form an enaminoketone of the formula

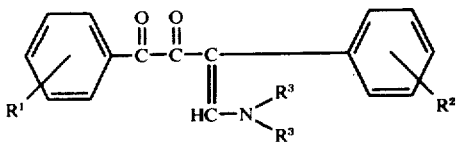

and contacting the enaminoketone with a hydrazine of the formula R—NHNH₂, or a hydrate of hydrohalide thereof, at a temperature from about 0° C. to about 40° C. in a second inert reaction solvent.

Each step of the above process is, in itself, a process new to the organic chemical art.

DESCRIPTION OF THE PREFERRED EMBODIMENT

The pyridazinones described above, wherein R represents $C_1$–$C_3$ alkyl, are useful herbicides. The compounds wherein R represents hydrogen are not herbicidally active, but are readily N-alkylated to form the herbicidal compounds.

In the above formula, the term $C_1$–$C_3$ alkyl is used to refer to such substituent groups as methyl, ethyl and isopropyl. The term hydrohalide refers to hydrochloride, hydrobromide, hydroiodide and hydrofluoride.

The following compounds, exemplary of those which are prepared by the process of this invention, are presented merely to assure that those of skill in the art understand the usefulness of the invention. Only 1-alkyl compounds, wherein R represents alkyl, are named here; it will be clear to those skilled in the art that the process is equally useful for preparing similar 1-unsubstituted compounds.

1-methyl-5-phenyl-3-(α,α,α-trifluoro-o-tolyl)-4(1H)-pyridazinone 1-ethyl-3-(3-fluorophenyl)-5-phenyl-4-(1H)-pyridazinone 1-methyl-3-phenyl-5-(α,α,α-trifluoro-p-tolyl)-4(1H)-pyridazinone 5-(2-chlorophenyl)-3-phenyl-1-propyl-4(1H)-pyridazinone 1-ethyl-5-(3-fluorophenyl)-3-phenyl-4(1H)-pyridazinone 1-isopropyl-5-phenyl-3-(α,α,α-trifluoro-m-tolyl)-4(1H)-pyridazinone 3-(2-chlorophenyl)-5-phenyl-1-propyl-4(1H)-pyridazinone 1-ethyl-3-(2-fluorophenyl)-5-phenyl-4(1H)-pyridazinone 3-(4-chlorophenyl)-1-methyl-5-(α,α,α-trifluoro-m-tolyl)-4(1H)-pyridazinone 5-(3-chlorophenyl)-1-methyl-3-phenyl-4(1H)-pyridazinone 3-(3-chlorophenyl)-5-(4-fluorophenyl)-1-methyl-4(1H)-pyridazinone 5-phenyl-1-propyl-3-(m-tolyl)-4(1H)-pyridazinone 3-(3-bromophenyl)-1-ethyl-5-phenyl-4(1H)-pyridazinone 3-(4-fluorophenyl)-5-phenyl-1-propyl-4(1H)-pyridazinone 5-(4-bromophenyl)-1-isopropyl-3-phenyl-4(1H)-pyridazinone 5-(4-chlorophenyl)-1-methyl-3-phenyl-4(1H)-pyridazinone 1-ethyl-3-(m-tolyl)-5-(α,α,α-trifluoro-m-tolyl)-4(1H)-pyridazinone 1-isopropyl-5-phenyl-3-(p-tolyl)-4(1H)-pyridazinone 5-(3-fluorophenyl)-1-methyl-3-($\alpha,\alpha,\alpha$-trifluoro-p-tolyl)-4(1H)-pyridazinone 3-(2-bromophenyl)-5-phenyl-1-propyl-4(1H)-pyridazinone 5-(3-bromophenyl)-1-ethyl-3-phenyl-4-(1H)-pyridazinone 1-ethyl-5-(m-tolyl)-3-($\alpha,\alpha,\alpha$-trifluoro-o-tolyl)-4(1H)-pyridazinone 5-(3-bromophenyl)-3-(2-chlorophenyl)-1-methyl-4(1H)-pyridazinone 1-methyl-3-phenyl-5-(o-tolyl)-4(1H)-pyridazinone 5-(2-chlorophenyl)-1-methyl-3-($\alpha,\alpha,\alpha$-trifluoro-m-tolyl)-4(1H)-pyridazinone 5-(4-chlorophenyl)-1-ethyl-3-(3-fluorophenyl)-4(1H)-pyridazinone 3-phenyl-1-propyl-5-(m-tolyl)-4(1H)-pyridazinone 5-(3-bromophenyl)-1-ethyl-3-(o-tolyl)-4(1H)-pyridazinone 5-(4-bromophenyl)-1-isopropyl-3-($\alpha,\alpha,\alpha$-trifluoro-m-tolyl)-4(1H)-pyridazinone 5-(4-fluorophenyl)-1-methyl-3-(o-tolyl)-4(1H)-pyridazinone 3-(3-bromophenyl)-5-(4-chlorophenyl)-1-methyl-4(1H)-pyridazinone 3-(4-chlorophenyl)-1-ethyl-5-(m-tolyl)-4(1H)-pyridazinone As is known in the art, the phenylglyoxyloyl halides which are starting compounds here are made from correspondingly substituted acetophenones by oxidizing the ketone with an agent such as potassium permanganate to form the corresponding glyoxylic acid. (Cf. Cymerman-Craig, *Australian J. Chem.* 9, 222 (1956)). The acid is then reacted with a halogenating agent to form the desired glyoxyloyl halide. The styrylamine starting compounds are readily made by the amination of an appropriately ring-substituted phenylacetaldehyde with a secondary amine bearing the $R^3$ substituents, according to the method of Mannich et. al., *Chem. Ber.* 69, 2106 (1936).

The $R^1$ and $R^2$ substituents are not affected by and do not affect the reaction, and are therefore readily provided by corresponding substituents of the starting compounds.

It will be clear to organic chemists that the $R^3$ substituents may be small alkyl groups, or may be combined to form a heterocyclic ring, as is economical or convenient in any given instance. The reaction goes well in either case.

The first step of the process is performed in the presence of a base, which serves as a proton scavenger. The term "base" here refers to tertiary amines and alkali metal carbonates and hydroxides. Such tertiary amines as pyridine, triethylamine, diazabicyclononane, diazabicycloundecane and the like are useful in the process. Carbonates and hydroxides of sodium, potassium and lithium are also used. The amount of the base is not critical. However, at least one equivalent of base is needed for each equivalent of enaminoketone to be produced; excess base is not harmful.

Both steps of the reaction are carried out in an inert reaction solvent. The identity of the solvent is by no means critical to the reaction. Any solvent which will dissolve the reactants, and which is inert in the sense that it does not react with the reactants or product of the step in which it is used, is satisfactory. It has been found that the preferred solvent in the first step is diethyl ether, and the preferred solvent in the second step comprises a mixture of diethyl ether and a $C_1$-$C_3$ alkanol such as methanol, ethanol or isopropanol. However, the same solvent can be used in both steps if it is convenient to do so.

The reaction goes at least acceptably well in other solvents, including aromatic solvents, aliphatic solvents, halogenated solvents, alcohols, carboxamides, and ethers in general. For example, the following are exemplary inert reaction solvents.

butanol
methanol
diisopropyl ether
tetrahydrofuran
ethyl propyl ether
methylene chloride
chloroform
ethylene dichloride
benzene
xylene
toluene
ethylbenzene
hexane
octane
cyclohexane
cyclohexanol
isooctane
dimethylformamide
1,2-dimethoxyethane Mixtures of various combinations of the above solvents are also satisfactory reaction solvents for this process.

Both steps of the process are best carried out at temperatures from about 0° C. to about 40° C., but can be performed at temperatures both below and above that range. The lower and upper boundaries of the named range are set more by convenience than by absolute criticality of the temperatures. As usual, the speed of the reaction decreases as the temperature is lowered. The desired product is produced at reaction temperatures below 0° C., but reaction at such low temperatures is undesirably slow.

As would be expected, reaction at a temperature above 40° C. increases the speed of the reaction. Higher temperatures, however, tend to produce undesired side reactions. Some of the reactants also tend to be unstable at elevated temperatures. The upper limit of the optimum temperature range of the reaction is therefore placed at 40° C. in both steps of the process.

As will be clear to organic chemists, operation of the process at temperatures both above and below the named optimum range will, nevertheless, at times be a desirable practice.

The hydrazines which are reactants in the process include such readily-obtainable compounds as hydrazine, hydrazine hydrate, hydrazine hydrochloride, hydrazine hydrobromide, methylhydrazine, methylhydrazine hydrate, propylhydrazine, propylhydrazine hydrate, and ethylhydrazine hydrochloride. Such hydrazines are presently obtainable and readily prepared by known methods.

As organic chemists will understand, the time during which each step of the reaction is carried out is variable, depending upon the individual characteristics of the specific reactants in use, and upon the reaction temperature. In general, reaction times from about one to about 24 hours are used in each of the two steps. It will be understood that at least a minimal amount of the desired product will be produced in each step even though an extremely brief reaction time is used.

When alkylhydrazines are used as reactants in the second step of the process, the products are 1-alkyl-pyridazinones, which are herbicides as explained below. The same compounds are also prepared, however, by using hydrazine (R=H) in the process, and using the 1-unsubstituted pyridazinones as intermediates for the preparation of the corresponding 1-alkyl compounds. Alkylation of the 1-unsubstituted pyridazinones is performed according to the common methods. It is usually preferred to alkylate with an alkyl halide in the presence of sodium hydride in dimethylformamide. Such alkylations are also commonly performed, however, with dialkyl sulfates in the presence of inorganic bases.

The above general description is believed to be adequate to enable a skilled organic chemist to perform the process of this invention. The following preparative examples, however, are presented to assure that the reader will have no difficulty in the use of the present invention. The first example illustrates the first step of the process.

EXAMPLE 1

1-diethylamino-2,4-diphenyl-1-buten-3,4-dione

Seven grams of N,N-diethylstyrylamine was dissolved in 100 ml. of diethyl ether and the solution was cooled to 0° C. Four grams of anhydrous triethylamine was added. A 7 g. portion of phenylglyoxyloyl chloride was dissolved in 50 ml. of diethyl ether and the solution was added dropwise, with stirring, to the first solution over about 75 minutes. As soon as the addition was complete, the reaction mixture was filtered, and the precipitated amine hydrochloride was washed with an additional 50 ml. of diethyl ether. The filtrate contained 1-diethylamino-2,4-diphenyl-1-buten-3,4-dione, in dissolved form, and was used in the next step of the synthesis without purification.

The following examples illustrate the preparation of pyridazinones by the second step of the process of this invention.

EXAMPLE 2

3,5-diphenyl-4(1H)-pyridazinone

The product solution from Example 1 was cooled to 0° C. and mixed with 20 ml. of isopropyl alcohol and 2 ml. of hydrazine. The mixture was stirred for 10 minutes, and was then warmed to room temperature and stirred for 15 hours. The product was then collected by filtration. The yield was 6.0 g. of 3,5-diphenyl-4(1H)-pyridazinone, m.p. 328°–32° C., which was identified by infrared and nuclear magnetic resonance analysis.

EXAMPLE 3

1-methyl-3,5-diphenyl-4(1H)-pyridazinone

A diethyl ether solution of the diphenyl enaminoketone intermediate was produced by following exactly the procedure of Example 1. To the cool solution was added 2 ml. of methylhydrazine, and the mixture was stirred overnight. The solution was then washed with 2N HCl, with 2N KOH, and with water, and was then dried over anhydrous magnesium sulfate. It was then evaporated under vacuum to produce 1.05 g. of 1-methyl-3,5-diphenyl-4(1H)-pyridazinone m.p. 165°–67° C., which was identified by nuclear magnetic resonance analysis.

The next examples illustrate the alkylation of 1-unsubstituted pyridazinones.

EXAMPLE 4

1-ethyl-3,5-diphenyl-4(1H)-pyridazinone

A 1 g. portion of the product of Example 2 was suspended in 40 ml. of dimethylformamide, the suspension was cooled under nitrogen to 0°–5° C., and an 0.3 g. portion of 50% NaH in oil was added. The reaction mixture was stirred for 30 minutes, and 3 ml. of ethyl iodide was added. The mixture was stirred at 0°–5° C. for 24 hours, and the mixture was then filtered to separate the precipitated product. The dried product was 1.0 g. of 1-ethyl-3,5-diphenyl-4(1H)-pyridazinone, m.p. 124°–25° C., which was identified by nuclear magnetic resonance analysis, infrared analysis, and mass spectrometry.

EXAMPLE 5

3,5-diphenyl-1-propyl-4(1H)-pyridazinone

Propyl iodide was reacted with 3,5-diphenyl-4(1H)-pyridazinone according to the process of Example 4 to produce 3,5-diphenyl-1-propyl-4(1H)-pyridazinone, m.p. 94°–96° C. in 95% yield.

The next two examples illustrate further typical syntheses using this invention.

EXAMPLE 6

3-(4-bromophenyl)-1-methyl-5-phenyl-4(1H)-pyridazinone

A 1.4 g. portion of (4-bromophenyl)glyoxyloyl chloride was dissolved in 50 ml. of diethyl ether. A 1.06 g. portion of diethylstyrylamine was dissolved in 10 ml. of diethyl ether, 1 ml. of triethylamine was added, and the mixture was cooled to 0° C. The glyoxyloyl chloride solution was added, and the reaction mixture was stirred at 0° C. for 2 hours. After the reaction period, the reaction mixture was filtered, and 5 ml. of isopropanol and 0.5 ml. of hydrazine were added to the filtrate. The mixture was stirred overnight at room temperature, and in the morning the product was separated by filtration. The yield was 1.2 g. of 3-(4-bromophenyl)-5-phenyl-4-(1H)-pyridazinone, m.p. higher than 300° C., which was identified by infrared, nuclear magnetic resonance, and mass spectrometry techniques.

A 1 g. portion of the intermediate above was dissolved in 40 ml. of dimethylformamide, and 0.3 g. of 50% sodium hydride oil dispersion added while the solution stirred at 0° C. After 30 minutes, 3 ml. of methyl iodide was added. The mixture was stirred at 0°–5° C. for 24 hours, and the product was recovered by filtration and recrystallized from hexane-isopropanol. The yield was 0.95 g. of 3-(4-bromophenyl)-1-methyl-5-phenyl-4(1H)-pyridazinone, m.p. 159°–60° C., which was identified by infrared, nuclear magnetic resonance and mass spectrometry analyses.

EXAMPLE 7

1-methyl-5-phenyl-3-($\alpha,\alpha,\alpha$-trifluoro-m-tolyl)-4(1H)-pyridazinone A 3.5 g. portion of (3-trifluoromethylphenyl)-glyoxyloyl chloride was dissolved in 50 ml. of diethyl ether. The solution was added dropwise to a mixture of 2.59 g. of diethylstyrylamine and 2 ml. of triethylamine in 50 ml. of diethyl ether at 0° C. After the addition, the mixture was stirred for 2 hours. One hundred ml. of methanol and 2 ml. of anhydrous hydrazine were then added, and the mixture was stirred for 6 hours more. Filtration of the reaction mixture gave 2.8 g. of 5-phenyl-3-($\alpha,\alpha,\alpha$-trifluoro-m-tolyl)-4(1H)-pyridazinone.

A 0.8 g. portion of the above intermediate was suspended in 30 ml. of water containing 2 g. of potassium hydroxide. The mixture was chilled to 0° C., 2 ml. of dimethyl sulfate was added, and the mixture was stirred for 24 hours. The mixture was then filtered, and the precipitate was washed with water and air dried. The dried product was 0.4 g. of 1-methyl-5-phenyl-3-($\alpha,\alpha,\alpha$-trifluoro-m-tolyl)-4(1H)-pyridazinone, m.p. 110°–12° C., which was identified by infrared, nuclear magnetic resonance, and mass spectrometry analyses.

The 1-alkyl pyridazinones made by the process described herein, or made by alkylating the 1-hydrogen compounds made by the process described herein, are herbicides and may be used for both preemergence and postemergence control of weeds. For example, application of typical compounds to soil in which seeds of large crabgrass, pigweed, foxtail, velvetleaf and morningglory were germinating inhibited or prevented the emergence of the weeds. Control the same weeds was also obtained by application of the compounds to the foliage of the growing weeds.

I claim:

1. A process for making compounds of the formula

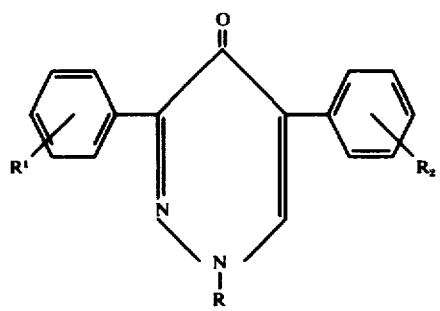

wherein R represents hydrogen or $C_1$–$C_3$ alkyl, and $R^1$ and $R^2$ independently represent trifluoromethyl, hydrogen, fluoro, chloro, bromo or methyl, which process comprises contacting a glyoxyloyl halide of the formula

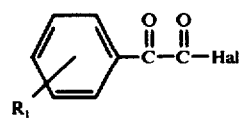

wherein Hal represents fluoro, chloro or bromo, with a styrylamine of the formula

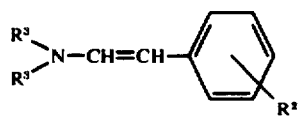

wherein the $R^3$ groups independently represent $C_1$–$C_3$ alkyl, or the $R^3$ groups combine with the nitrogen atom to which they are attached to form azetidino, pyrrolidino, piperidino, or morpholino, at a temperature from about 0° C. to about 40° C. in an inert reaction solvent in the presence of at least one equivalent per equivalent of product of a base chosen from the group consisting of tertiary amines and alkali metal carbonates and hydroxides to form an enaminoketone of the formula

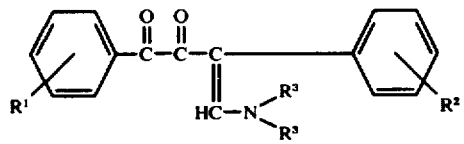

and contacting the enaminoketone with a hydrazine of the formula R—NHNH$_2$, or a hydrate or hydrohalide thereof, at a temperature from about 0° C. to about 40° C. in a second inert reaction solvent.

2. A process of claim 1 wherein the second inert reaction solvent comprises a mixture of diethyl ether and a $C_1$–$C_3$ alkanol.

3. A process for making compounds of the formula

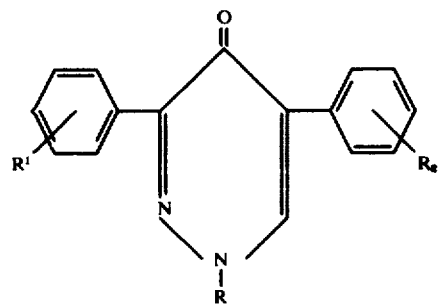

wherein R represents hydrogen or $C_1$–$C_3$ alkyl, and $R^1$ and $R^2$ independently represent trifluoromethyl, hydrogen, fluoro, chloro, bromo or methyl, which process comprises contacting an enaminoketone of the formula

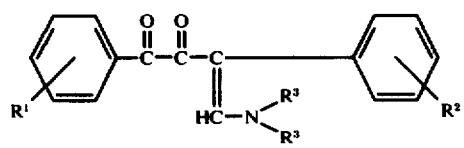

wherein the $R^3$ groups independently represent $C_1$–$C_3$ alkyl, or the $R^3$ groups combine with the nitrogen atom to which they are attached to form azetidino, pyrrolidino, piperidino or morpholino with a hydrazine of the formula R–NHNH$_2$, or a hydrate or hydrohalide thereof, at a temperature from about 0° C. to about 40° C. in an inert reaction solvent.

4. A process of claim 3 wherein the inert reaction solvent comprises a mixture of diethyl ether and a $C_1$–$C_3$ alkanol.

* * * * *